(12) United States Patent
Minami et al.

(10) Patent No.: US 8,293,782 B2
(45) Date of Patent: Oct. 23, 2012

(54) COMPOUND, PROBE CONTAINING THE NOVEL COMPOUND, AND FLUORESCENCE-IMAGING CONTRAST AGENT CONTAINING THE NOVEL COMPOUND OR THE PROBE

(75) Inventors: Masato Minami, Yokohama (JP); Yoshinori Tomida, Atsugi (JP); Atsushi Takahashi, Kawasaki (JP); Kouichi Kato, Yokohama (JP); Fumiko Tomatsu, Yokohama (JP); Sachiko Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 18 days.

(21) Appl. No.: 12/696,496

(22) Filed: Jan. 29, 2010

(65) Prior Publication Data

US 2010/0197937 A1     Aug. 5, 2010

(30) Foreign Application Priority Data

Jan. 30, 2009   (JP) ................. 2009-020244
Jun. 8, 2009    (JP) ................. 2009-137346

(51) Int. Cl.
  *A61K 31/403*   (2006.01)
  *C07D 209/10*   (2006.01)

(52) U.S. Cl. ........................ 514/415; 548/455

(58) Field of Classification Search .......... 548/455; 514/415
See application file for complete search history.

(56) References Cited

U.S. PATENT DOCUMENTS

| | | | |
|---|---|---|---|
| 5,968,479 A | 10/1999 | Ito | |
| 6,027,709 A * | 2/2000 | Little et al. | 424/1.65 |
| 6,083,485 A | 7/2000 | Licha | |
| 6,258,340 B1 | 7/2001 | Licha et al. | |
| 6,913,743 B2 | 7/2005 | Licha | |
| 7,488,468 B1 | 2/2009 | Miwa | |
| 7,547,721 B1 | 6/2009 | Miwa | |

FOREIGN PATENT DOCUMENTS

| | | |
|---|---|---|
| JP | 09-127115 A | 5/1997 |
| JP | 2001-511195 T | 8/2001 |
| JP | 2002-526458 T | 8/2002 |
| JP | 2005-120026 A | 5/2005 |
| JP | 2005-232190 A | 9/2005 |
| WO | 2002-26891 A1 | 4/2002 |

OTHER PUBLICATIONS

Mader et al, Bioconjugate Chemistry (2004), vol. 15, pp. 70-78.*

* cited by examiner

*Primary Examiner* — Kamal Saeed
*Assistant Examiner* — Janet L Coppins
(74) *Attorney, Agent, or Firm* — Canon U.S.A., Inc., IP Division

(57) ABSTRACT

A compound represented by Formula (1) below,

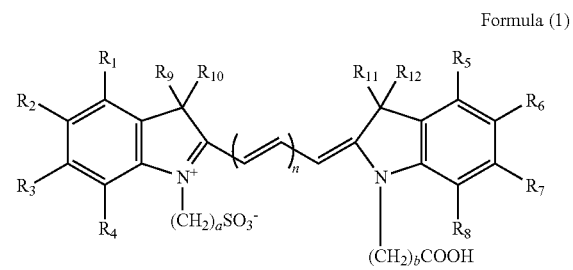

Formula (1)

where n is 2 or 3; a is an integer of 1 to 4 and b is an integer of 3 and 5 to 10, or a is 5 and b is an integer of 1 to 10; $R_1$ to $R_8$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; and $R_9$ to $R_{12}$ each independently represent a substituted or unsubstituted C1-C3 alkyl group.

16 Claims, 9 Drawing Sheets

COMPOUND, PROBE CONTAINING THE NOVEL COMPOUND, AND FLUORESCENCE-IMAGING CONTRAST AGENT CONTAINING THE NOVEL COMPOUND OR THE PROBE

BACKGROUND OF THE INVENTION

1. Field of the Invention

The present invention relates to a novel compound, a probe containing such a novel compound, and a contrast agent for fluorescence imaging, the contrast agent containing such a novel compound or such a probe.

2. Description of the Related Art

When a disease is treated, it is considerably important to recognize variations caused in a body (biological system) at an initial stage of the disease. In particular, visualization of the locations and the size of tumors by diagnostic imaging provides considerably useful data for diagnosing or treating the disease. Such visualization can be achieved by an existing technique such as fluorescence imaging, ultrasonic imaging, photoacoustic imaging, X-ray imaging, MRI (magnetic resonance imaging), CT imaging (computerized tomography imaging), or PET (positron emission tomography).

Fluorescence imaging is conducted by radiating near-infrared light having relatively high transmittance through biological tissues to a biological system to thereby excite a contrast agent that has been administered to the biological system in advance, and detecting fluorescence emission from the contrast agent in the biological system. Thus, visualization of the locations and the size of tumors can be achieved. Dyes that absorb light in the near-infrared region and emit fluorescence in the near-infrared region are used as such contrast agents for fluorescence imaging. Among such dyes, a cyanine dye has been prominently studied in recent years (WO2002/026891).

WO2002/026891 discloses a compound in which a molecule (capture molecule) selectively binding to a target site is fixed to a cyanine dye molecule with a peptide bond between the capture molecule and the cyanine dye molecule. However, such a cyanine dye compound has a problem of being slowly discharged from biological systems. Specifically, when a cyanine dye compound in which capture molecules are fixed with peptide bonds is administered to a biological system, an enzyme in the biological system may cleave the peptide bonds. As a result of such cleavage of the peptide bonds, cyanine dye molecules without the capture molecules become present in a large amount in portions other than the target sites. Thus, when the target sites are subjected to fluorescence imaging, fluorescence emission from such sole cyanine dye molecules becomes background emission, which can cause degradation of measurement sensitivity. Accordingly, there has been a demand for the development of a dye that is rapidly discharged from biological systems, that is, a dye that is cleared rapidly (having rapid clearance).

SUMMARY OF THE INVENTION

The present invention provides a novel compound that is rapidly discharged from biological systems, a probe containing such a novel compound, and a contrast agent for fluorescence imaging, the contrast agent containing such a novel compound or such a probe.

A compound according to a first aspect of the present invention is represented by Formula (1) below.

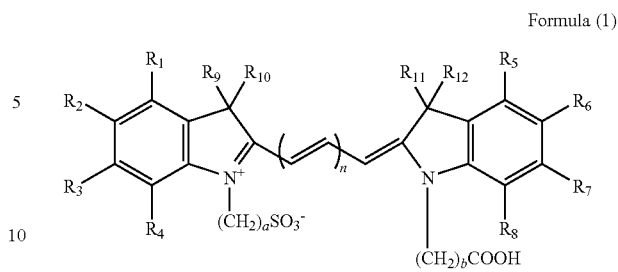

Formula (1)

In Formula (1), n is 2 or 3; a is an integer of 1 to 4 and b is an integer of 3 and 5 to 10, or a is 5 and b is an integer of 1 to 10; $R_1$ to $R_8$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; and $R_9$ to $R_{12}$ each independently represent a substituted or unsubstituted C1-C3 alkyl group.

A compound according to a second aspect of the present invention is represented by Formula (2) below.

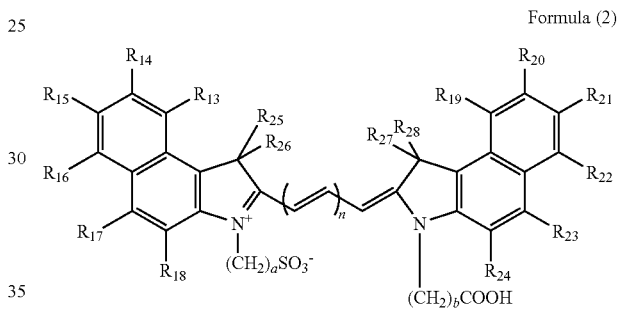

Formula (2)

In Formula (2), n is 2 or 3; a is an integer of 1 to 4 and b is an integer of 3 and 5 to 10, or a is 5 and b is an integer of 1 to 10 (however, a case where n is 2, a is 4, and b is 5; a case where n is 3, a is 3, and b is 5; and a case where n is 3, a is 4, and b is 5 are excluded.); $R_{13}$ to $R_{24}$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; and $R_{25}$ to $R_{28}$ each independently represent a substituted or unsubstituted C1-C3 alkyl group.

A probe according to a third aspect of the present invention is represented by Formula (3) below.

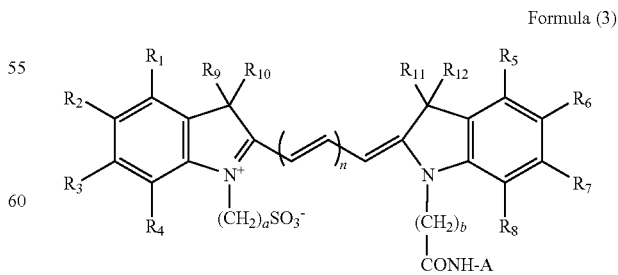

Formula (3)

In Formula (3), n is 2 or 3; a and b each represent an integer of 1 to 10; $R_1$ to $R_8$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; $R_9$ to $R_{12}$ each independently represent a substituted or unsubstituted C1-C3 alkyl group; and A represents a labeled substance.

A probe according to a fourth aspect of the present invention is represented by Formula (4) below.

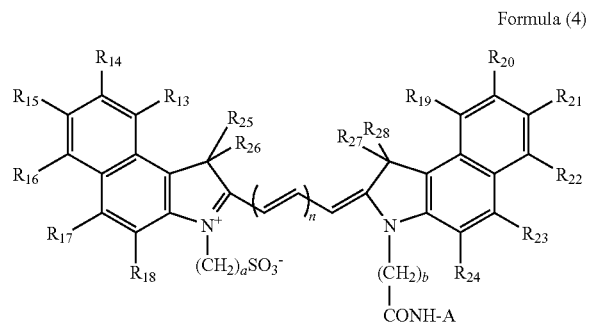

Formula (4)

In Formula (4), n is 2 or 3; a and b each represent an integer of 1 to 10; $R_{13}$ to $R_{24}$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; $R_{25}$ to $R_{28}$ each independently represent a substituted or unsubstituted C1-C3 alkyl group; and A represents a labeled substance.

A compound according to a fifth aspect of the present invention is represented by Formula (5) below.

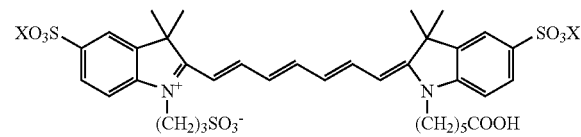

Formula (5)

In Formula (5), each $SO_3X$ represents any one of sodium sulfonate, potassium sulfonate, ammonium sulfonate, triethylammonium sulfonate, pyridinium sulfonate, lysine sulfonate, and arginine sulfonate.

A compound according to a sixth aspect of the present invention is represented by Formula (6) below.

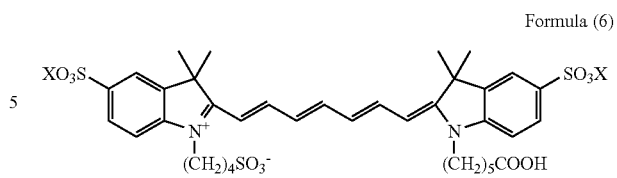

Formula (6)

In Formula (6), each $SO_3X$ represents any one of sodium sulfonate, potassium sulfonate, ammonium sulfonate, triethylammonium sulfonate, pyridinium sulfonate, lysine sulfonate, and arginine sulfonate.

A compound according to a seventh aspect of the present invention is represented by Formula (7) below.

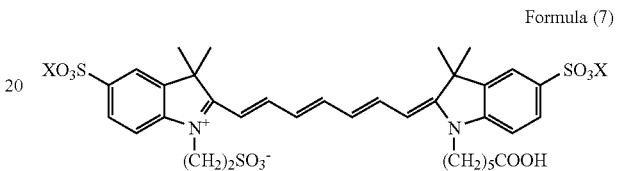

Formula (7)

In Formula (7), each $SO_3X$ represents any one of sodium sulfonate, potassium sulfonate, ammonium sulfonate, triethylammonium sulfonate, pyridinium sulfonate, lysine sulfonate, and arginine sulfonate.

A compound according to an eighth aspect of the present invention is represented by Formula (8) below.

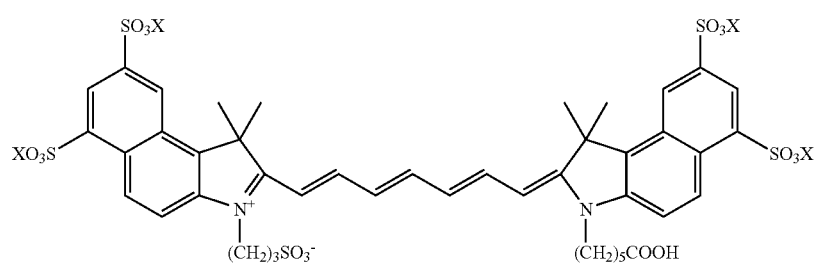

Formula (8)

In Formula (8), each $SO_3X$ represents any one of sodium sulfonate, potassium sulfonate, ammonium sulfonate, triethylammonium sulfonate, pyridinium sulfonate, lysine sulfonate, and arginine sulfonate.

The present invention provides a novel compound that is rapidly discharged from biological systems compared with existing compounds.

A novel compound according to the present invention is considerably suitable as a labeling agent for fluorescence imaging.

Further features of the present invention will become apparent from the following description of exemplary embodiments with reference to the attached drawings.

DESCRIPTION OF THE EMBODIMENTS

Figure 1:
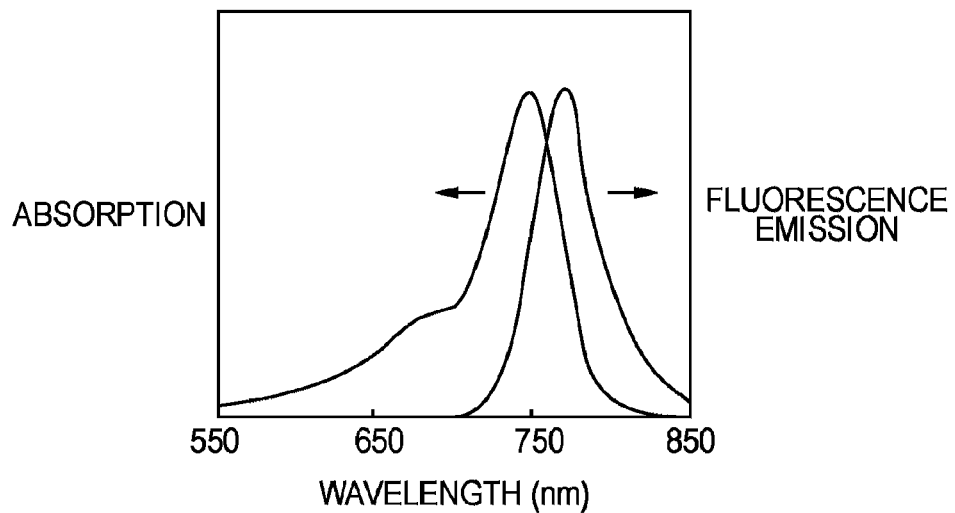
FIG. 1 is a graph showing the absorption spectrum and the fluorescence spectrum of the compound represented by Formula (5-1) according to an embodiment of the present invention.

Hereinafter, embodiments of the present invention will be described.
Clearance

A compound according to an embodiment of the present invention is desirably discharged more rapidly from a biological system after administration of the compound to the biological system and desirably remains in the biological system in a smaller amount. This is because the load on the biological system thereby becomes smaller. When the compound is discharged rapidly from the biological system, fluorescence imaging with the compound can be followed by a test, a treatment, or the like in which another contrast agent, a therapeutic agent, or the like is administered, which is desirable.

Stated another way, with reference to the fluorescence intensity on the surface of a biological system before administration of the compound, the fluorescence intensity desirably decreases to a lower level in a shorter time after the administration.

Specifically, a compound according to an embodiment desirably satisfies the following conditions. When the fluorescence intensity on the surface of a biological system before administration of the compound to the biological system is defined as 0.08 and the fluorescence intensity on the surface of the biological system after the lapse of 15 minutes from the administration of the compound to the biological system is defined as 1, the fluorescence intensity on the surface of the biological system desirably decreases to 0.2 or less within 24 hours from the administration of the compound to the biological system.
Maximum Fluorescence Wavelength A compound according to an embodiment desirably has a maximum fluorescence wavelength of 600 nm or more in the near-infrared region in view of transmittance of the emitted fluorescence through biological systems, more desirably in the range of 680 to 850 nm.
Maximum Absorption Wavelength A compound according to an embodiment desirably has a maximum absorption wavelength of 600 nm or more in the near-infrared region in view of transmittance of radiated light through biological systems, more desirably in the range of 680 to 850 nm.
Molar Absorptivity A compound according to an embodiment desirably has a molar absorptivity of 100,000 or more. This is because such a compound absorbs more light and, as a result, the intensity of fluorescence emitted increases. More desirably, the molar absorptivity is 200,000 or more.

Hereinafter, embodiments of the present invention will be described in detail.
First Embodiment
Structural Formula An example of a compound according to an embodiment is represented by Formula (1) below.

Formula (1)

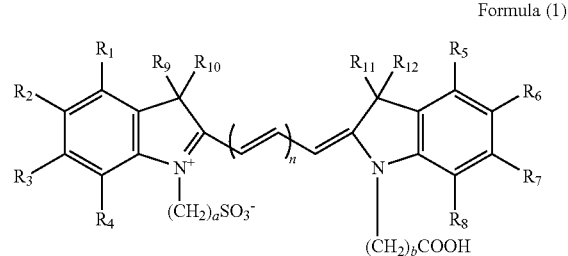

In Formula (1), n is 2 or 3; and a is an integer of 1 to 4 and b is an integer of 3 and 5 to 10, or a is 5 and b is an integer of 1 to 10. $R_1$ to $R_8$ each independently represent a hydrogen atom or a sulfonate. The sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed. $R_9$ to $R_{12}$ each independently represent a substituted or unsubstituted C1-C3 alkyl group. Examples of the alkyl group include a methyl group, an ethyl group, a propyl group, and an isopropyl group. Such an alkyl group may be substituted with a hydroxyl group, a sulfonate, or the like. This sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

Clearance

A compound represented by Formula (1) above desirably satisfies the following condition. When the fluorescence intensity on the surface of a biological system before administration of the compound to the biological system is defined as 0.08 and the fluorescence intensity on the surface of the biological system after the lapse of 15 minutes from the administration of the compound to the biological system is defined as 1, the fluorescence intensity on the surface of the biological system decreases to 0.1 or less within 24 hours from the administration of the compound to the biological system. More desirably, the fluorescence intensity on the surface of the biological system decreases to 0.1 or less within 3 hours from the administration of the compound to the biological system.

Synthesis Scheme

A compound represented by Formula (1) above can be synthesized, for example, with reference to Bioconjugate Chem. 105 (1993). A synthesis scheme for the compound is shown below.

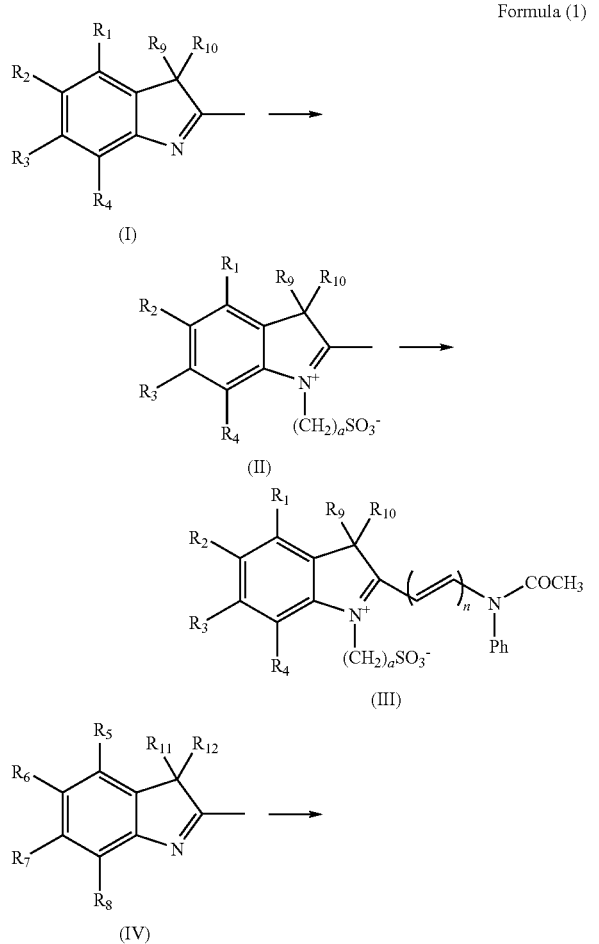

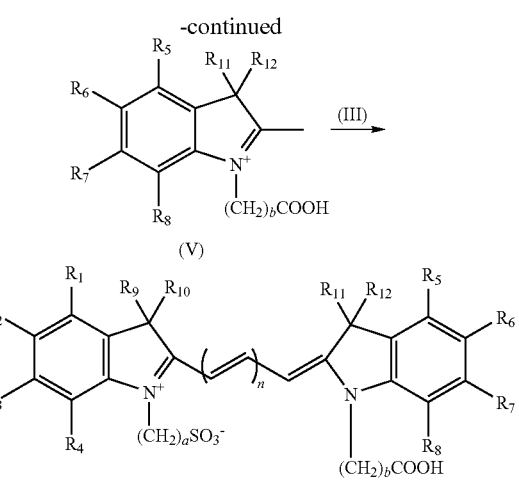

First, a sulfoalkyl group is introduced into an indole (I) to thereby synthesize an indole derivative (II). Second, a methine chain is introduced into the indole derivative (II) to thereby synthesize an indole derivative (III). When n is 2, the methine chain is introduced with malonaldehyde dianil hydrochloride. When n is 3, the methine chain is introduced with glutaconaldehyde dianil hydrochloride.

A carboxyalkyl group is then introduced into an indole (IV) to thereby synthesize an indole derivative (V). The indole derivative (V) is subsequently coupled with the indole derivative (III) to thereby provide a target compound represented by Formula (1).

Examples of compounds that satisfy the above-described desirable conditions in terms of clearance, maximum fluorescence wavelength, maximum absorption wavelength, and molar absorptivity include compounds represented by Formulae (5) to (7) below.

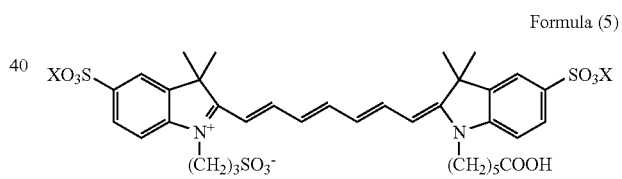

Formula (5)

In Formula (5), each $SO_3X$ represents any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

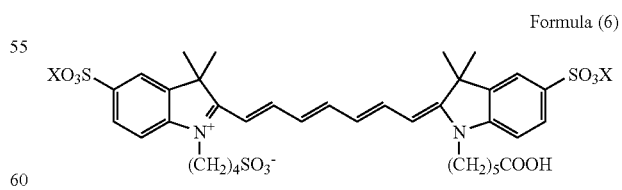

Formula (6)

In Formula (6), each $SO_3X$ represents any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

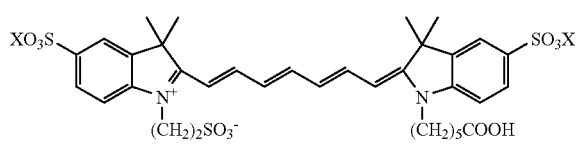

Formula (7)

In Formula (7), each $SO_3X$ represents any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

Second Embodiment

Structural Formula

An example of a compound according to another embodiment of the present invention is represented by Formula (2) below.

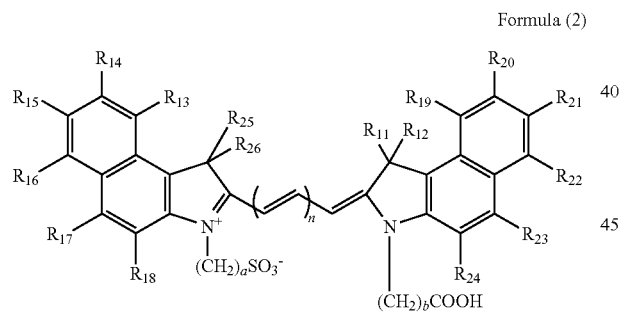

Formula (2)

In Formula (2), n is 2 or 3; and a is an integer of 1 to 4 and b is an integer of 3 and 5 to 10, or a is 5 and b is an integer of 1 to 10 (however, the case where n is 2, a is 4, and b is 5; the case where n is 3, a is 3, and b is 5; and the case where n is 3, a is 4, and b is 5 are excluded.). $R_{13}$ to $R_{24}$ each independently represent a hydrogen atom or a sulfonate. The sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed. $R_{25}$ to $R_{28}$ each independently represent a substituted or unsubstituted C1-C3 alkyl group. Examples of the alkyl group include a methyl group, an ethyl group, a propyl group, and an isopropyl group. Such an alkyl group may be substituted with a hydroxyl group, a sulfonate, or the like. This sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

Synthesis Scheme

A compound represented by Formula (2) above can be synthesized in a manner similar to the synthesis scheme of a compound represented by Formula (1) above.

Examples of compounds that satisfy the above-described desirable conditions in terms of clearance, maximum fluorescence wavelength, maximum absorption wavelength, and molar absorptivity include compounds represented by Formula (8) below.

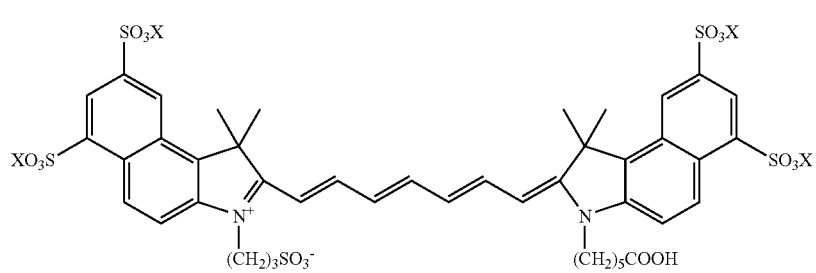

Formula (8)

In Formula (8), each $SO_3X$ represents any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

Third Embodiment

Probe

A probe that contains a labeled substance (described below) being fixed to a compound represented by Formula (1) above with a peptide bond between the substance and the compound is represented by Formula (3) below.

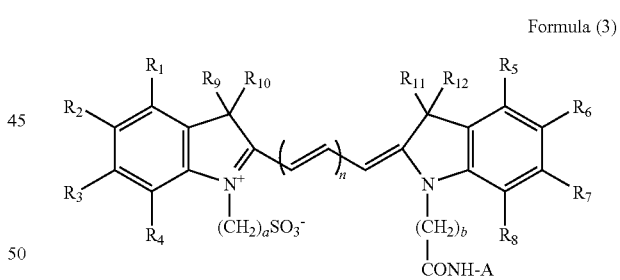

Formula (3)

In Formula (3), n is 2 or 3; and a and b each represent an integer of 1 to 10. $R_1$ to $R_8$ each independently represent a hydrogen atom or a sulfonate. The sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed. $R_9$ to $R_{12}$ each independently represent a substituted or unsubstituted C1-C3 alkyl group. Examples of the alkyl group include a methyl group, an ethyl group, a propyl group, and an isopropyl group. Such an alkyl group may be substituted with a hydroxyl group, a sulfonate, or the like. This sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed. A represents a labeled substance.

A probe represented by Formula (3) above has selectivity for a target site and hence the target site can be specifically detected.

Fourth Embodiment

Probe

A probe that contains a labeled substance being fixed to a compound represented by Formula (2) above with a peptide bond between the substance and the compound is represented by Formula (4) below.

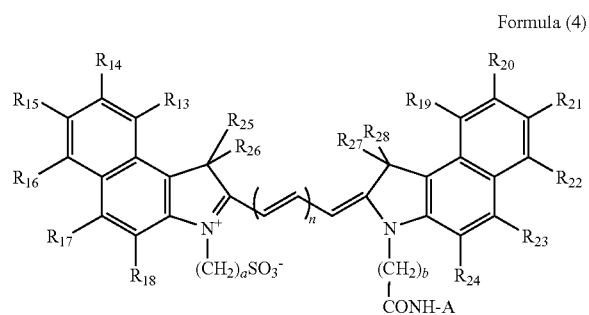

Formula (4)

In Formula (4), n is 2 or 3; and a and b each represent an integer of 1 to 10. $R_{13}$ to $R_{24}$ each independently represent a hydrogen atom or a sulfonate. The sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed.

$R_{25}$ to $R_{28}$ each independently represent a substituted or unsubstituted C1-C3 alkyl group. Examples of the alkyl group include a methyl group, an ethyl group, a propyl group, and an isopropyl group. Such an alkyl group may be substituted with a hydroxyl group, a sulfonate, or the like. This sulfonate is any one of sodium sulfonate, potassium sulfonate, ammonium sulfonate, triethylammonium sulfonate, pyridinium sulfonate, lysine sulfonate, and arginine sulfonate. However, these sulfonates are not limitative and another pharmaceutically acceptable sulfonate may be employed. A represents a labeled substance.

A probe represented by Formula (4) above has selectivity for a target site and hence the target site can be specifically detected.

Labeled Substance

A labeled substance in the present invention is, for example, a substance specifically binding to a target site such as a tumor or a substance specifically binding to a substance present around a target site, and is freely selected from, for example, biomolecules and chemical substances such as pharmaceuticals. Specifically, an example of such a labeled substance is an antibody, an antibody fragment, an enzyme, a biologically active peptide, a glycopeptide, a sugar chain, a lipid, or a molecular recognition compound. In a probe according to the present invention, a labeled substance is chemically bonded to a compound represented by Formula (1), (2), (5), (6), (7), or (8) with a carboxyl group of the compound between the labeled substance and the compound. Use of such a probe enables specific detection of a target site, or tracking of kinetics, localization, potency, metabolism, or the like of a target substance.

Method for Fixing Substance to be Labeled

Such a substance to be labeled (hereinafter, sometimes referred to as a label substance) can be fixed to a compound represented by Formula (1), (2), (5), (6), (7), or (8), for example, in the following manner in the present invention. The carboxyl group of the compound is substituted, using N-hydroxysulfosuccinimide (NHS), 1-ethyl-3-(3-dimethylaminopropyl)carbodiimide (EDC), or the like, to provide a succinimide group, which is a reactive ester group. By effecting reaction between the resultant succinimide group (reactive ester group) and an amino group of a label substance, the label substance can be fixed.

Alternatively, a label substance can also be fixed to a compound represented by Formula (1), (2), (5), (6), (7), or (8) in the following manner in the present invention. The carboxyl group of the compound is substituted to provide a succinimide group and subsequently turned into a maleimide group. By effecting reaction between the resultant maleimide group and a thiol group of a label substance having the thiol group or a label substance modified to have the thiol group, the label substance can be fixed. Alternatively, another method may also be used.

Labeling Agent for Fluorescence Imaging

A compound and a probe according to the present invention have a maximum fluorescence wavelength and a maximum absorption wavelength of 600 nm or more in the near-infrared region and hence absorb light that passes through biological systems to a high degree and emit fluorescence that passes through biological systems to a high degree. Accordingly, such a compound and a probe are suitable as a contrast agent for fluorescence imaging.

A compound and a probe according to the present invention can also be used as a contrast agent for a photonic imaging such as photoacoustic imaging.

The contrast agent for fluorescence imaging and the contrast agent for photonic imaging (a contrast agent for photoacoustic imaging or the like) can be used in the form of a solution obtained by dissolving or dispersing the contrast agent in a solvent such as a physiological saline solution or distilled water for injection. If necessary, the solution containing the contrast agent may be appropriately mixed with a pharmaceutically acceptable additive. Such a contrast agent can be introduced into a biological system by injection, administration via a percutaneous, subcutaneous, or intrabronchial route.

Imaging Method

An imaging method using a compound according to the present invention (an imaging method according to the present invention) includes two steps described below. Note that an imaging method according to the present invention may further include another step.

Step (1): administering a compound or a probe according to the present invention to a biological system Step (2): radiating light to the biological system and detecting fluorescence emitted from the compound or the probe according to the present invention in the biological system Regarding Step (1)

The compound according to the present invention is a compound represented by Formula (1), (2), (5), (6), (7), or (8) above. When such a compound is used, sites where blood vessels are densely packed such as tumor sites contain a larger amount of the compound than other sites. Thus, tumor sites can be located and the size and the like of the tumor sites can also be determined.

The probe according to the present invention is a compound represented by Formula (3) or (4) above. When such a probe is used, by appropriately selecting a labeled substance contained in the probe, various target sites can be specifically detected. For example, when a substance specifically binding to tumors is selected as the labeled substance, tumors can be specifically detected with the probe. When a substance specifically binding to a biological substance present in a large amount in a lesion region, such as a protein or an enzyme, is selected as the labeled substance, the lesion region can be specifically detected with the probe.

The term "biological system" comprehensively refers to biological systems including animals, such as human beings and mice, and cells taken from living organisms.

Regarding Step (2)

The light radiated to a biological system desirably has a wavelength of 600 nm or more in the near-infrared region. Such light highly transmits through biological systems. An apparatus for emitting such light and an apparatus for detecting fluorescence are not particularly restricted and can be appropriately selected from various apparatuses.

An imaging method in which a compound according to the present invention is used can be performed by conducting the above-described Steps (1) and (2) to thereby image target sites such as tumors. Thus, the imaging method has the following advantages.

First, since the diameter of tumors can be determined only by conducting the above-described Steps (1) and (2), the need for special apparatuses is eliminated and the imaging method can be readily performed. Second, compared with the existing method in which the diameter of tumors of mice is determined by measuring lump sites (tumor sites) with vernier calipers, use of the imaging method enables simple and accurate measurement of the diameter of tumors and reduces the degree to which measured values of the diameter of tumors depend on the individual performing the measurement.

Third, as will be demonstrated in Examples below, since a compound according to the present invention is rapidly discharged from biological systems, the compound puts less load on biological systems, the load being caused by the compound remaining in the biological systems for a long period of time. Additionally, without a long time interval, an imaging method according to the present invention can be immediately followed by another test, a treatment, or the like in which another contrast agent or the like is administered. Examples of such another contrast agent include paramagnetic materials, magnetic particles, nuclear magnetic resonance-active nuclei that are used for detection by nuclear magnetic resonance; radionuclides such as $^{123}$I, $^{201}$Tl, $^{67}$Ga, $^{99m}$Tc, and $^{111}$In that are used for γ counter detection; and compounds and probes that contain, for example, positron emission nuclides such as $^{15}$O, $^{13}$N, $^{11}$C, and $^{18}$F. A medicament or the like for treatment can be administered in accordance with the size of the detected lesion site such as a tumor. Another test such as nuclear magnetic resonance (NMR), magnetic resonance imaging (MRI), or positron emission tomography (PET) can be performed with such another contrast agent.

EXAMPLES

Hereinafter, the present invention will be described in further detail with reference to examples. However, the present invention is not restricted to these examples. In the following descriptions, NMR analysis was performed with AVANCE 500 (manufactured by Bruker Corporation); MS analysis was performed with Q-Tof Ultima (manufactured by Waters Corporation); and fluorescence imaging was performed with IVIS (trademark) Imaging System (manufactured by Caliper Life Sciences, Inc.).

Example 1

Synthesis of Compound Represented by Formula (5)

A compound represented by Formula (5) was synthesized by the following synthesis scheme.

The reaction between potassium indolemonosulfonate (I) (2.5 g, manufactured by TRC Biomedical Research Chemicals) and 1,3-propanesultone (2.0 g, manufactured by TOKYO CHEMICAL INDUSTRY CO., LTD.) was effected in toluene (30 ml) at 110° C. for 24 hours. After the reaction was complete, the resultant reaction solution was cooled to room temperature and toluene was then removed from the reaction solution. After that, the resultant reaction residue was washed with diethyl ether several times. Thus, a compound (II) was obtained.

The reaction between the compound (II) (1.4 g) and gluta-conaldehyde dianil hydrochloride (1.0 g) was subsequently effected in acetic anhydride (18 ml) and acetic acid (9 ml) at 120° C. for 3 hours. After the reaction was complete, the resultant reaction solution was cooled to room temperature and subsequently crystallized by being slowly added dropwise to ethyl acetate. The ethyl acetate was then removed from the resultant solution and a compound (III) was obtained.

The reaction between potassium indolemonosulfonate (I) (1.5 g) and 6-bromohexanoic acid (1.3 g, manufactured by TOKYO CHEMICAL INDUSTRY CO., LTD.) was effected in toluene (20 ml) for 24 hours. After the reaction was complete, the resultant reaction solution was cooled to room temperature and toluene was then removed from the reaction solution. After that, the resultant reaction residue was washed with diethyl ether several times. Thus, a compound (IV) was obtained.

The reaction between the compound (III) (1.8 g) and the compound (IV) (1.1 g) was subsequently effected in acetic anhydride (18 ml) and pyridine (9 ml) at 110° C. for 20 minutes. After the reaction was complete, the resultant reaction solution was cooled to room temperature and subsequently crystallized by being slowly added dropwise to ethyl acetate. The ethyl acetate was then removed from the resultant solution and the crystallized substance was separated and purified with TLC RP-C18 (manufactured by Merck Ltd.) (developer: water/methanol=1/1). Thus, the compound represented by Formula (5-1) below was obtained. The absorption spectrum and the fluorescence spectrum of the compound represented by Formula (5-1) are shown in FIG. 1.

Synthesis Scheme

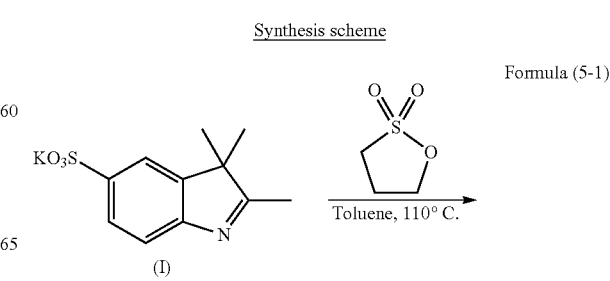

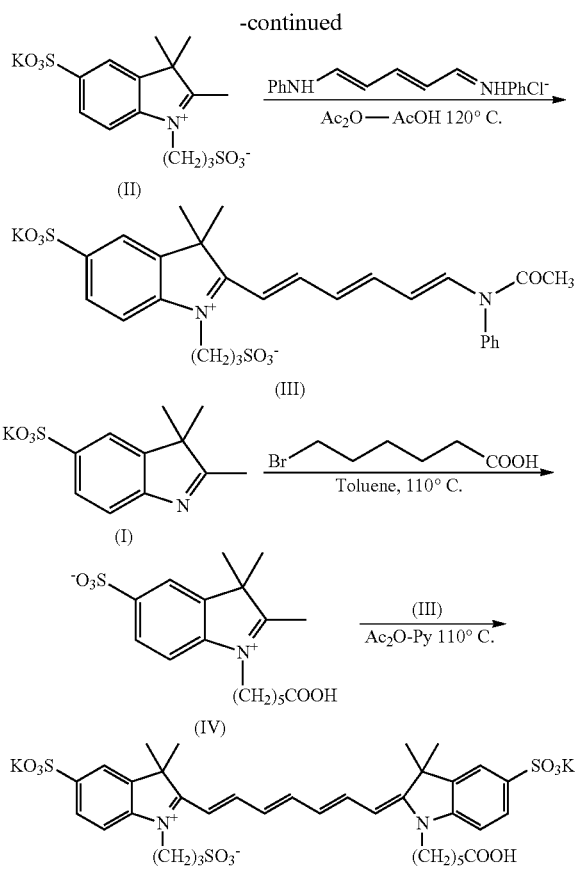

Data of the compound represented by Formula (5-1):

NMR (500 MHz, deuterium oxide) δ/ppm 1.33-1.39(m, 2H), 1.58(s, 6H), 1.57(s, 6H), 1.54-1.63(m, 2H), 1.73-1.79 (m, 2H), 2.15 (t, 2H, J=7.0 Hz), 2.99(t, 2H, J=7.0 Hz), 4.03(t, 2H), 4.11(t, 2H, J=7.0 Hz), 6.14(d, 1H, J=13.5 Hz), 6.19(d, 1H, J=13.5 Hz), 6.34-6.44(m, 2H), 7.19(d, 1H, J=8.5 Hz), 7.28(d, 1H, J=8.5 Hz), 7.33-7.45(m, 1H), 7.73(s, 1H), 7.78(s, 1H), 7.67(d, 1H, J=8.5 Hz), 7.75-7.86(m, 2H), 7.72(d, 1H, J=8.5 Hz)

MS (ESI, positive mode) 777.21778 [M+3H−2K]$^+$ Exact MS: 777.21855

Maximum absorption wavelength ($H_2O$)=747 nm
Maximum fluorescence wavelength ($H_2O$)=768 nm
Molar absorptivity ($H_2O$)=246000

Example 2

Synthesis of Compound Represented by Formula (6)

A compound represented by Formula (6) was synthesized by the following synthesis scheme.

The reaction between potassium indolemonosulfonate (I) (2.0 g) and 1,4-butanesultone (1.2 g, manufactured by TOKYO CHEMICAL INDUSTRY CO., LTD.) was effected in toluene (15 ml) at 110° C. for 24 hours. After the reaction was complete, the resultant reaction solution was cooled to room temperature and toluene was then removed from the reaction solution. After that, the resultant reaction residue was washed with diethyl ether several times. Thus, a compound (V) was obtained.

The reaction between the compound (V) (0.7 g) and glutaconaldehyde dianil hydrochloride (0.5 g) was subsequently effected in acetic anhydride (16 ml) and acetic acid (8 ml) at 120° C. for 3 hours. After the reaction was complete, the resultant reaction solution was cooled to room temperature and subsequently crystallized by being slowly added dropwise to ethyl acetate. The ethyl acetate was then removed from the resultant solution and a compound (VI) was obtained.

Figure 2:
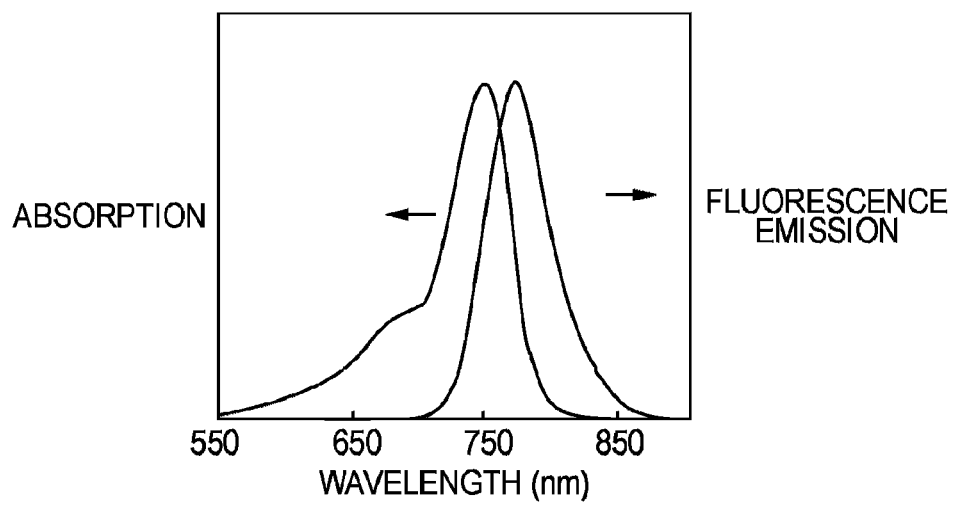
FIG. 2 is a graph showing the absorption spectrum and the fluorescence spectrum of the compound represented by Formula (6-1) according to an embodiment of the present invention.

The reaction between the compound (VI) (0.5 g) and the compound (IV) (0.3 g) was subsequently effected in acetic anhydride (14 ml) and pyridine (7 ml) at 110° C. for 20 minutes. After the reaction was complete, the resultant reaction solution was cooled to room temperature and subsequently crystallized by being slowly added dropwise to ethyl acetate. The ethyl acetate was then removed from the resultant solution and the crystallized substance was separated and purified with TLC RP-C18 (manufactured by Merck Ltd.) (developer: water/methanol=1/1). Thus, the compound represented by Formula (6-1) below was obtained. The absorption spectrum and the fluorescence spectrum of the compound represented by Formula (6-1) are shown in FIG. 2.

Synthesis Scheme

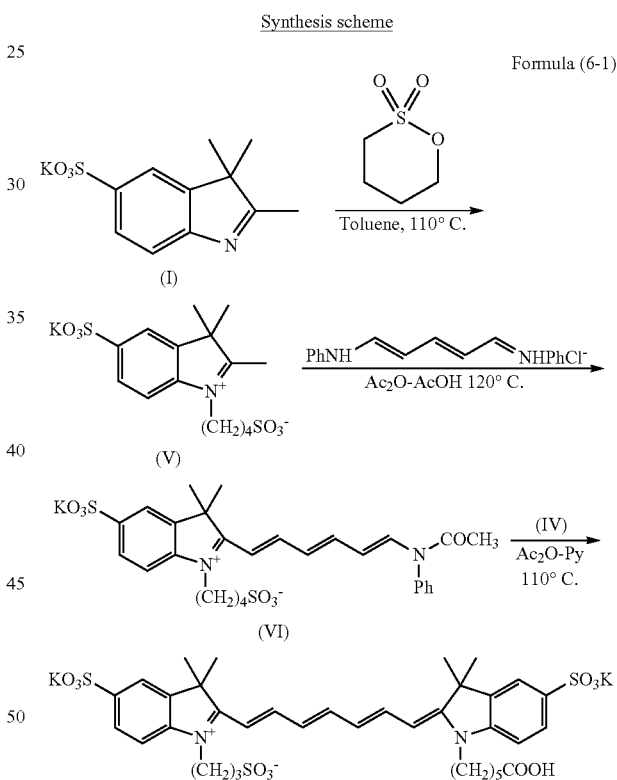

Data of the compound represented by Formula (6-1):

NMR (500 MHz, deuterium oxide) δ/ppm 1.37(q, 2H), 1.58(s, 6H), 1.59(s, 6H), 1.61(m, 2H), 1.75(t, 2H), 1.83-1.89 (m, 4H), 2.32(t, 2H), 2.92(t, 2H), 4.00(t, 4H), 6.14(m, 2H), 6.39(br, 2H), 7.23(d, 2H, J=8.0 Hz), 7.39(t, 1H), 7.71(d, 2H, J=8.0 Hz), 7.76(s, 2H), 7.76-7.89(m, 2H)

MS (ESI, positive mode) 791.2333 [M+3H−2K]$^+$ Exact MS: 791.23420

Maximum absorption wavelength ($H_2O$)=748 nm

Maximum fluorescence wavelength ($H_2O$)=772 nm

Molar absorptivity ($H_2O$)=242000

Example 3

Synthesis of Compound Represented by Formula (7)

A compound represented by Formula (7) was synthesized by the following synthesis scheme.

The reaction between potassium indolemonosulfonate (I) (2.0 g) and 2-chloroethanesulfonyl chloride (1.6 g, manufactured by TOKYO CHEMICAL INDUSTRY CO., LTD.) was effected in acetic acid (26 ml) at 120° C. for 9 hours. After the reaction was complete, the resultant reaction solution was cooled to room temperature and subsequently crystallized by being added to ethyl acetate. After that, the resultant crystallized substance was washed with ethyl acetate several times. Thus, a compound (VII) was obtained.

The reaction between the compound (VII) (1.2 g) and glutaconaldehyde dianil hydrochloride (0.9 g) was subsequently effected in acetic anhydride (16 ml) and acetic acid (8 ml) at 120° C. for 3 hours. After the reaction was complete, the resultant reaction solution was cooled to room temperature and subsequently crystallized by being slowly added dropwise to ethyl acetate. The ethyl acetate was then removed from the resultant solution and a compound (VIII) was obtained.

Figure 3:
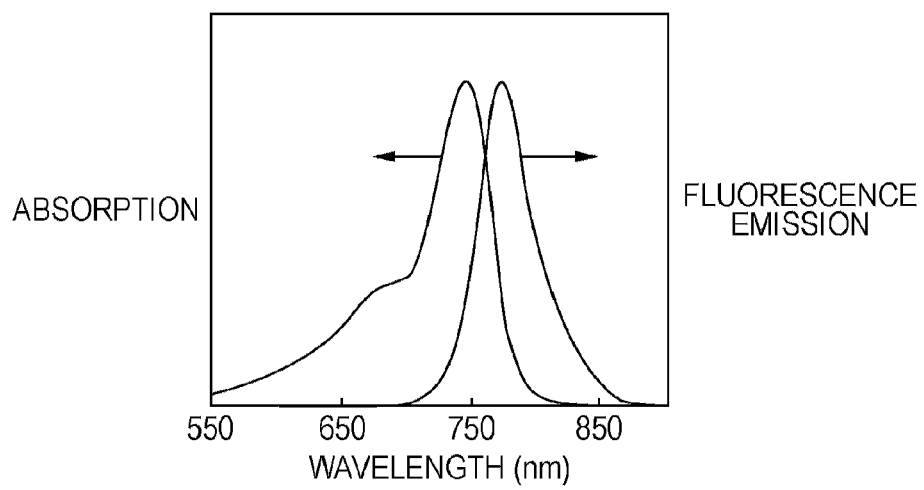
FIG. 3 is a graph showing the absorption spectrum and the fluorescence spectrum of the compound represented by Formula (7-1) according to an embodiment of the present invention.

The reaction between the compound (VIII) (0.6 g) and the compound (IV) (0.4 g) was subsequently effected in acetic anhydride (14 ml) and pyridine (7 ml) at 110° C. for 20 minutes. After the reaction was complete, the resultant reaction solution was cooled to room temperature and subsequently crystallized by being slowly added dropwise to ethyl acetate. The ethyl acetate was then removed from the resultant solution and the crystallized substance was separated and purified with TLC RP-C18 (manufactured by Merck Ltd.) (developer: water/methanol=1/1). Thus, the compound represented by Formula (7-1) below was obtained. The absorption spectrum and the fluorescence spectrum of the compound represented by Formula (7-1) are shown in FIG. 3.

Synthesis Scheme

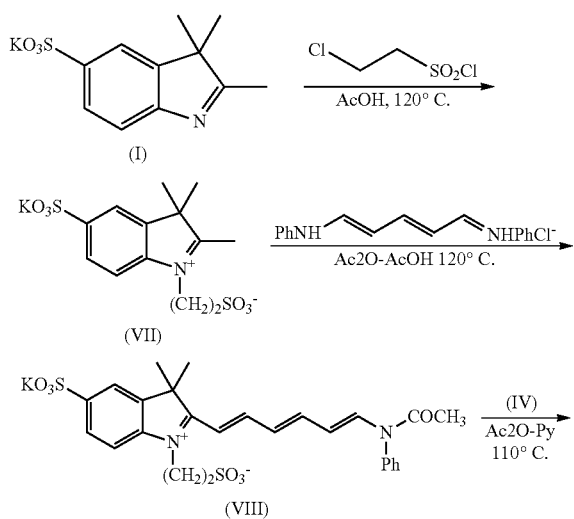

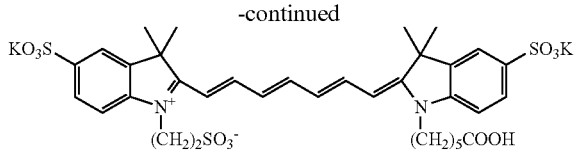

Data of the compound represented by Formula (7-1):

NMR (500 MHz, deuterium oxide) δ/ppm 1.38-1.46(m, 2H), 1.60-1.69(m, 2H), 1.64(s, 6H), 1.67(s, 6H), 1.80-1.87 (m, 2H), 2.32(t, 2H), 3.33(t, 2H), 4.13(br, 2H), 4.36(br, 2H), 6.15(d, 1H), 6.36(d, 1H), 6.54(q, 2H), 7.23(d, 1H, J=8.0 Hz), 7.40(d, 1H, J=8.0 Hz), 7.49(t, J=12.5 Hz, 1H, J=8.0 Hz), 7.75(d, 1H, J=8.0 Hz), 7.78(s, 1H), 7.80(br, 1H), 7.82(d, 1H, J=8.0 Hz), 7.87(s, 1H), 7.95(t, 1H, J=13.0 Hz)

MS (ESI, positive mode) 763.20244 [M+3H−2K]$^+$Exact MS: 763.20290

Maximum absorption wavelength ($H_2O$)=745 nm
Maximum fluorescence wavelength ($H_2O$)=773 nm
Molar absorptivity ($H_2O$)=207000

Example 4

Synthesis of Compound Represented by Formula (8)

A compound represented by Formula (8) was synthesized by the following synthesis scheme.

The reaction between potassium naphthylindoledisulfonate (VII) (1.5 g) and 1,3-propanesultone (0.6 g) was effected in toluene (15 ml) at 110° C. for 24 hours. After the reaction was complete, the resultant reaction solution was cooled to room temperature and toluene was then removed from the reaction solution. After that, the resultant reaction residue was washed with diethyl ether several times. Thus, a compound (VIII) was obtained.

The reaction between the compound (VIII) (1.0 g) and glutaconaldehyde dianil hydrochloride (0.5 g) was subsequently effected in acetic anhydride (18 ml) and acetic acid (9 ml) at 120° C. for 3 hours. After the reaction was complete, the resultant reaction solution was cooled to room temperature and subsequently crystallized by being slowly added dropwise to ethyl acetate. The ethyl acetate was then removed from the resultant solution and a compound (IX) was obtained.

The reaction between potassium naphthylindolemonosulfonate (VII) (1.0 g) and 6-bromohexanoic acid (1.2 g) was effected in toluene (18 ml) for 24 hours. After the reaction was complete, the resultant reaction solution was cooled to room temperature and toluene was then removed from the reaction solution. After that, the resultant reaction residue was washed with diethyl ether several times. Thus, a compound (X) was obtained.

Figure 4:
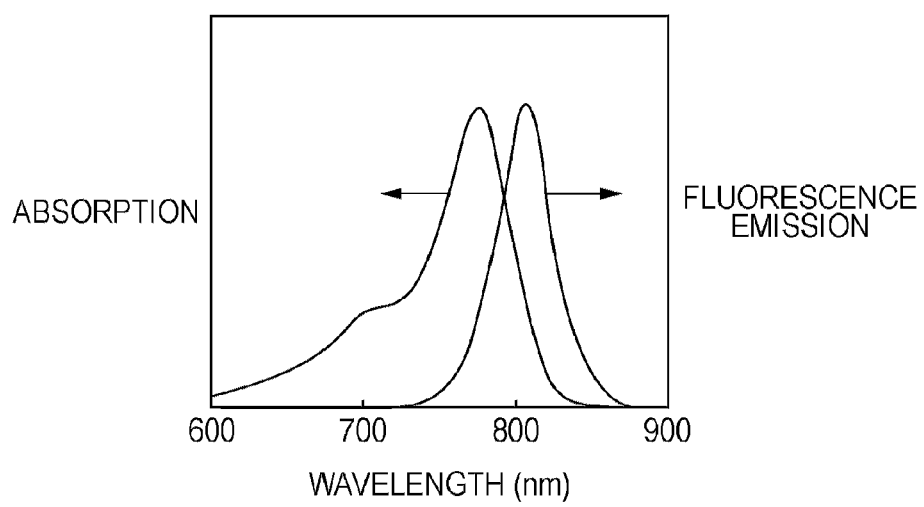
FIG. 4 is a graph showing the absorption spectrum and the fluorescence spectrum of the compound represented by Formula (8-1) according to an embodiment of the present invention.

The reaction between the compound (IX) (0.5 g) and the compound (X) (0.4 g) was subsequently effected in acetic anhydride (14 ml) and pyridine (7 ml) at 110° C. for 20 minutes. After the reaction was complete, the resultant reaction solution was cooled to room temperature and subsequently crystallized by being slowly added dropwise to ethyl acetate. The ethyl acetate was then removed from the resultant solution and the crystallized substance was separated and purified with TLC RP-C18 (manufactured by Merck Ltd.) (developer: water/methanol=1/1). Thus, the compound represented by Formula (8-1) below was obtained. The absorption spectrum and the fluorescence spectrum of the compound represented by Formula (8-1) are shown in FIG. 4.

Synthesis scheme

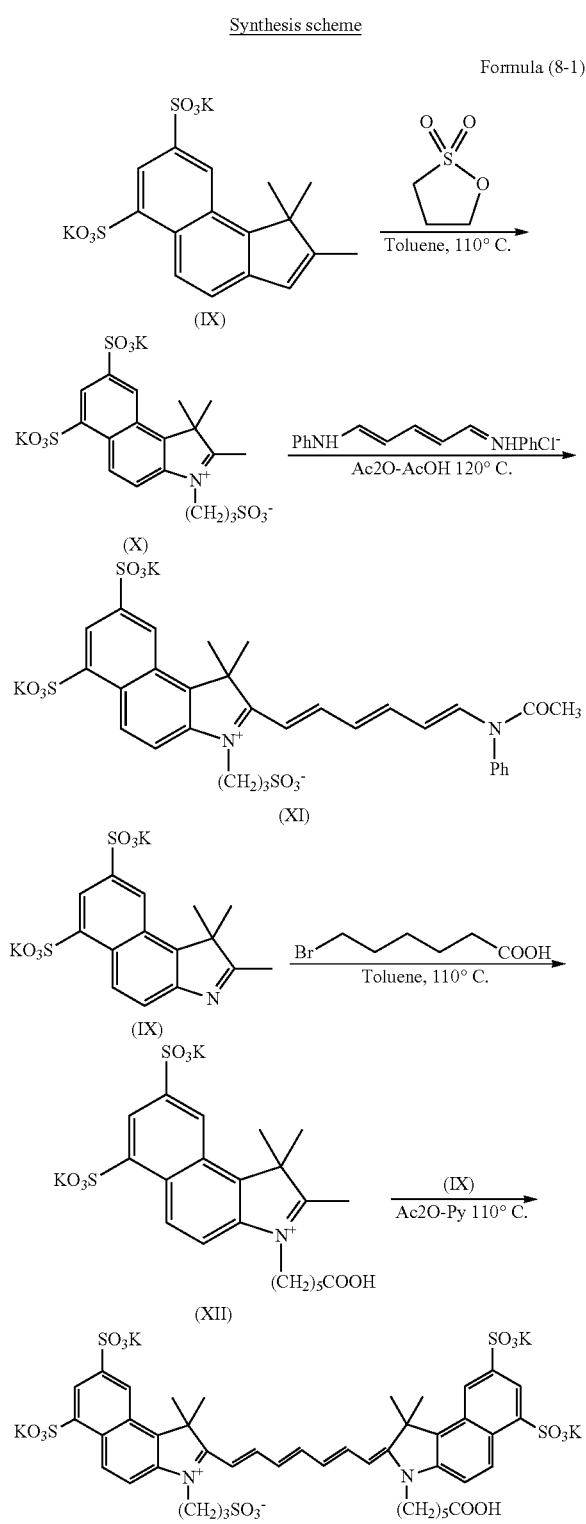

Data of the compound represented by Formula (8-1):

NMR (500 MHz, deuterium oxide) δ/ppm 1.37-1.44(m, 2H), 1.59(t, 2H), 1.80-1.90(m, 2H), 1.94(s, 12H), 2.29(t, 2H), 3.03(t, 2H), 4.18(t, 2H), 4.25(t, 2H), 6.26(d, 1H, J=11.0 Hz), 6.35(d, 1H, J=14.0 Hz), 6.51-6.62(m, 2H), 7.50-7.60(m, 1H), 7.74(d, 1H, J=9.0 Hz), 7.79(d, 1H, J=8.0 Hz), 7.98-8.08(m, 2H), 8.27(s, 1H), 8.32(s, 1H), 8.73-8.80(m, 4H)

MS (ESI, positive mode) 1037.16289 [M+5H−4K]$^+$ Exact MS: 1037.16348

Maximum absorption wavelength (H$_2$O)=776 nm
Maximum fluorescence wavelength (H$_2$O)=806 nm
Molar absorptivity (H$_2$O)=258000

Example 5

In Vivo Kinetics Evaluation 1

The compound represented by Formula (5-1) and synthesized in EXAMPLE 1 was evaluated in terms of in vivo kinetics with mice by fluorescence imaging. For comparative examples, Alexa Fluor (trademark) 750 (hereinafter, referred to as Reagent 1) and Alexa Fluor (trademark) 790 (hereinafter, referred to as Reagent 2) marketed by Molecular Probes, Inc. were used.

Figure 5:
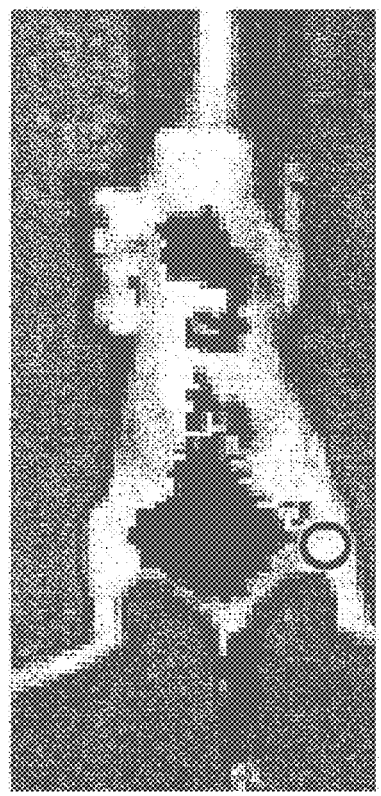
FIG. 5 is an image of a mouse used in in vivo kinetics evaluation of the compound represented by Formula (5-1) according to an embodiment of the present invention.

First, 200 μL PBS solutions (concentration: 5 μM) of the Formula (5-1) compound, Reagent 1, and Reagent 2 were intravenously injected into the tails of mice. Variation in fluorescence in a leg portion (circled portion in FIG. 5) of each mouse over time was evaluated with IVIS (trademark) Imaging System by measuring fluorescence intensity at 15 minutes, 1 hour, 3 hours, 5 hours, 7 hours, 24 hours, 48 hours, 72 hours, and 96 hours after the injection.

Figure 6A:
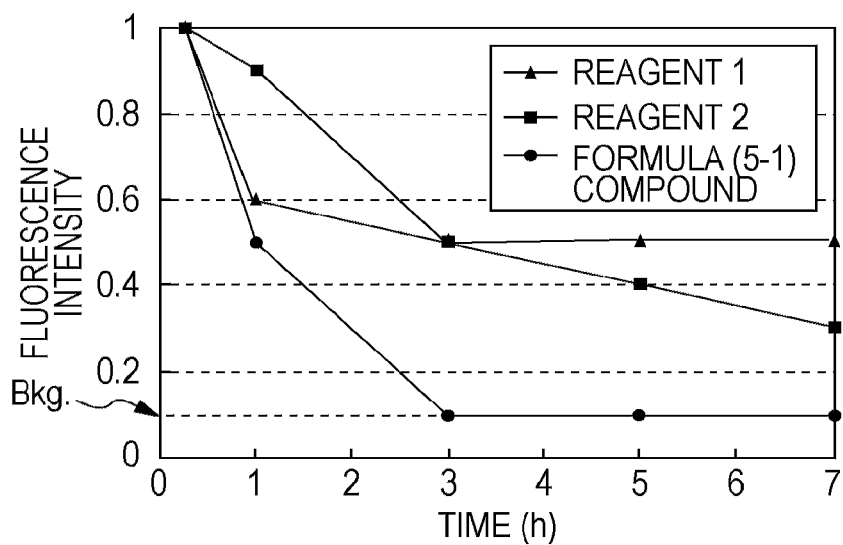
FIG. 6A is a graph showing variation in fluorescence intensity over time from administration of the compound represented by Formula (5-1) according to an embodiment of the present invention to a mouse to the lapse of 7 hours.
Figure 6B:
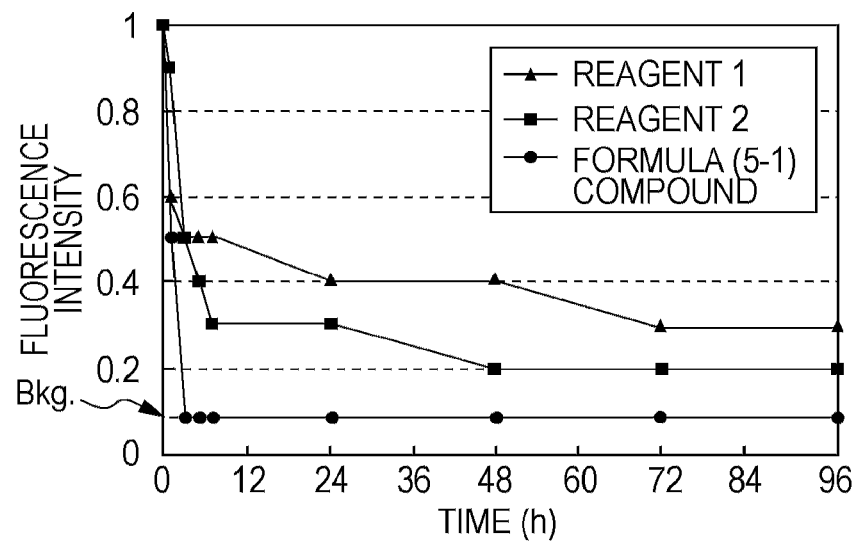
FIG. 6B is a graph showing variation in fluorescence intensity over time from administration of the compound represented by Formula (5-1) according to an embodiment of the present invention to a mouse to the lapse of 96 hours.

In this fluorescence measurement, the mice were anesthetized by inhalation. The evaluation was conducted after the NHS groups of Reagent 1 and Reagent 2 were deactivated with glycin. The results of variation in fluorescence intensity over time are shown in FIGS. 6A and 6B. In FIGS. 6A and 6B, the fluorescence intensity on the surface of each mouse before administration of each compound (background fluorescence emission, which is shown as Bkg. in FIGS. 6A and 6B) is defined as 0.08. The fluorescence intensity on the surface of each mouse after the lapse of 15 minutes from administration of each compound is defined as 1.

Referring to FIG. 6A, after the lapse of 3 hours from intravenous injection of the compound represented by Formula (5-1), the fluorescence intensity of the Formula (5-1) compound decreased to 0.08, which is the fluorescence intensity level before administration of the Formula (5-1) compound. This result suggests the possibility that the Formula (5-1) compound is rapidly discharged from biological systems compared with Reagent 1 and Reagent 2 serving as comparative examples.

Example 6

In Vivo Kinetics Evaluation 2

Figure 7:
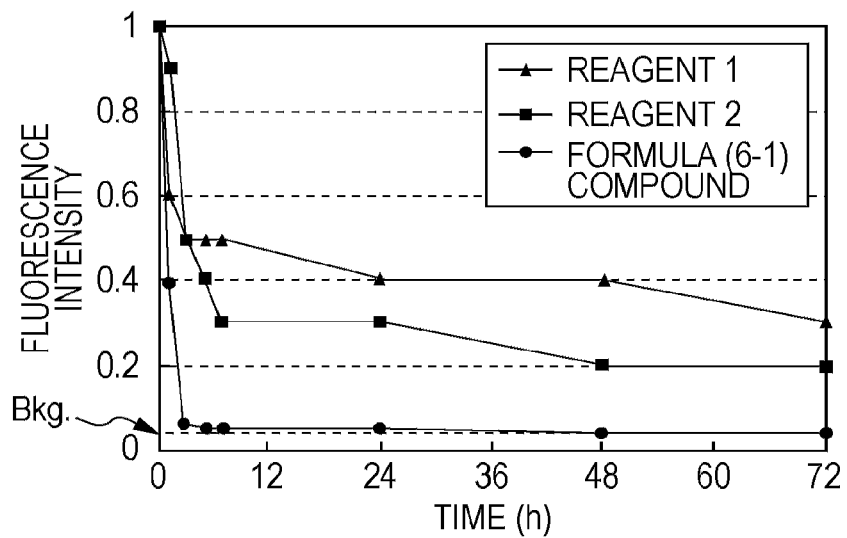
FIG. 7 is a graph showing variation in fluorescence intensity over time after administration of the compound represented by Formula (6-1) according to an embodiment of the present invention to a mouse.

The compound represented by Formula (6-1) and synthesized in EXAMPLE 2 was evaluated in terms of in vivo kinetics as in EXAMPLE 5. The results are shown in FIG. 7. Referring to FIG. 7, variation in fluorescence in leg portions of mice over time was evaluated by measuring fluorescence intensity at 15 minutes, 1 hour, 3 hours, 5 hours, 7 hours, 24 hours, 48 hours, and 72 hours after administration of the Formula (6-1) compound, Reagent 1, and Reagent 2 to the mice. In FIG. 7, the fluorescence intensity on the surface of each mouse before administration of each compound (background fluorescence emission, which is shown as Bkg. in FIG. 7) is defined as 0.05. The fluorescence intensity on the surface of each mouse after the lapse of 15 minutes from administration of each compound is defined as 1.

Referring to FIG. 7, after the lapse of 3 hours from intravenous injection of the compound represented by Formula (6-1), the fluorescence intensity of the Formula (6-1) compound decreased to 0.05, which is the fluorescence intensity level before administration of the Formula (6-1) compound.

This result suggests the possibility that the Formula (6-1) compound is rapidly discharged from biological systems compared with Reagent 1 and Reagent 2 serving as comparative examples.

Example 7

In Vivo Kinetics Evaluation 3

Figure 8:
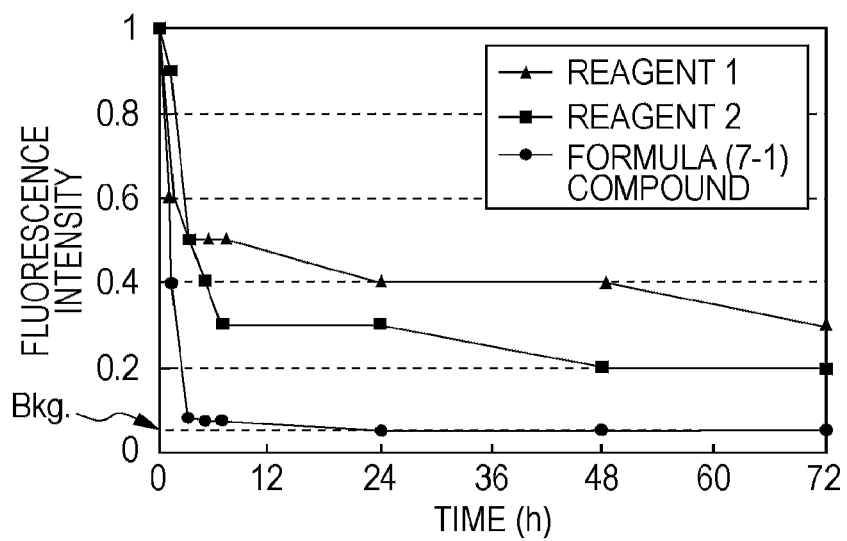
FIG. 8 is a graph showing variation in fluorescence intensity over time after administration of the compound represented by Formula (7-1) according to an embodiment of the present invention to a mouse.

The compound represented by Formula (7-1) and synthesized in EXAMPLE 3 was evaluated in terms of in vivo kinetics as in EXAMPLE 5. The results are shown in FIG. 8. Referring to FIG. 8, variation in fluorescence in leg portions of mice over time was evaluated by measuring fluorescence intensity at 15 minutes, 1 hour, 3 hours, 5 hours, 7 hours, 24 hours, 48 hours, and 72 hours after administration of the Formula (7-1) compound, Reagent 1, and Reagent 2 to the mice. In FIG. 8, the fluorescence intensity on the surface of each mouse before administration of each compound (background fluorescence emission, which is shown as Bkg. in FIG. 8) is defined as 0.05. The fluorescence intensity on the surface of each mouse after the lapse of 15 minutes from administration of each compound is defined as 1.

Referring to FIG. 8, after the lapse of 3 hours from intravenous injection of the compound represented by Formula (7-1), the fluorescence intensity of the Formula (7-1) compound decreased to 0.05, which is the fluorescence intensity level before administration of the Formula (7-1) compound. This result suggests the possibility that the Formula (7-1) compound is rapidly discharged from biological systems compared with Reagent 1 and Reagent 2 serving as comparative examples.

Example 8

In Vivo Kinetics Evaluation 4

Figure 9:
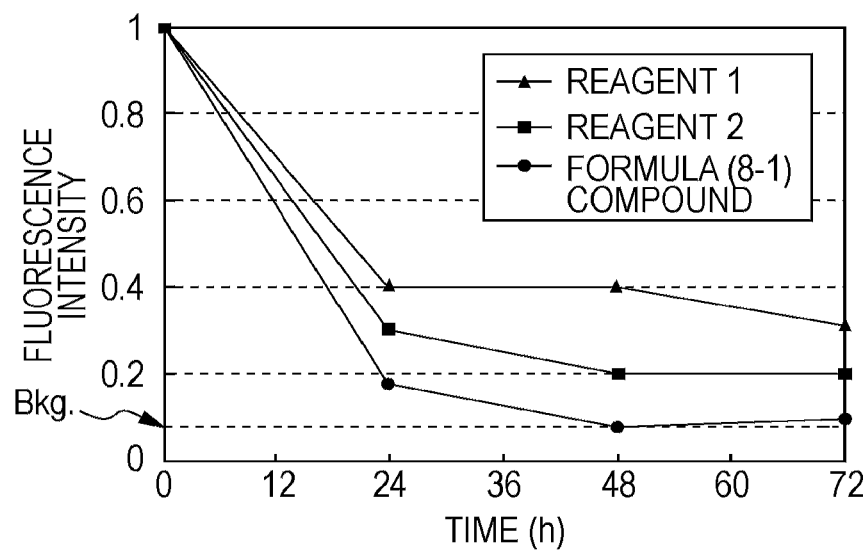
FIG. 9 is a graph showing variation in fluorescence intensity over time after administration of the compound represented by Formula (8-1) according to an embodiment of the present invention to a mouse.

The compound represented by Formula (8-1) and synthesized in EXAMPLE 4 was evaluated in terms of in vivo kinetics as in EXAMPLE 5. The results are shown in FIG. 9. Referring to FIG. 9, variation in fluorescence in leg portions of mice over time was evaluated by measuring fluorescence intensity at 15 minutes, 24 hours, 48 hours, and 72 hours after administration of the Formula (8-1) compound, Reagent 1, and Reagent 2 to the mice. In FIG. 9, the fluorescence intensity on the surface of each mouse before administration of each compound (background fluorescence emission, which is shown as Bkg. in FIG. 9) is defined as 0.08. The fluorescence intensity on the surface of each mouse after the lapse of 15 minutes from administration of each compound is defined as 1.

Referring to FIG. 9, the fluorescence intensity of the compound represented by Formula (8-1) decreased to 0.16 by the lapse of 24 hours from intravenous injection of the Formula (8-1) compound. This result suggests the possibility that the Formula (8-1) compound is rapidly discharged from biological systems compared with Reagent 1 and Reagent 2 serving as comparative examples.

Example 9

Fading Evaluation 1

The Formula (5-1) compound, Reagent 1, and Reagent 2, which were used in EXAMPLE 5, were evaluated in terms of fading by being dissolved in fetal bovine serum (FBS) and subsequently irradiated with an interior light having a luminance of 680 LUX. In this evaluation, the concentration of the Formula (5-1) compound, Reagent 1, and Reagent 2 was 5 µM. The results of the fading evaluation are shown in Table 1 below and FIG. 10. The ordinate of FIG. 10 indicates $\log(A_t/A_0)$ where $A_0$ and $A_t$ respectively represent absorbance at the maximum absorption wavelength after the lapse of 0 and t hours from the irradiation of the interior light. The fading rate in Table 1 is expressed by $(A_0-A_{24})/A_0$, that is, variation in absorbance at the maximum absorption wavelength after the lapse of 24 hours.

Figure 10:
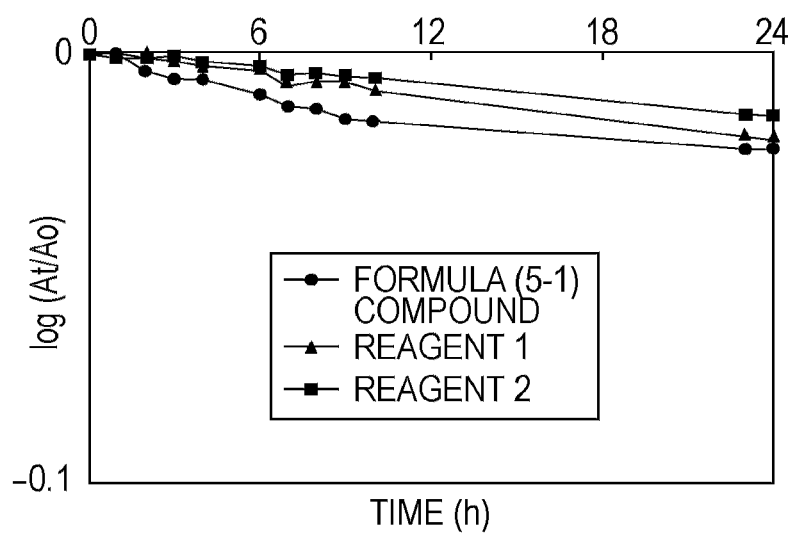
FIG. 10 is a graph showing the fading property of the compound represented by Formula (5-1) according to an embodiment of the present invention.

Referring to Table 1 and FIG. 10, the Formula (5-1) compound exhibited fading behavior similar to those of Reagent 1 and Reagent 2. This result suggests that the considerable decrease in the fluorescence intensity of the Formula (5-1) compound by the lapse of 3 hours from intravenous injection of the Formula (5-1) compound in EXAMPLE 5 is caused not by fluorescence fading but by rapid discharging of the Formula (5-1) compound from the biological system.

TABLE 1

| Compound | Fading rate (%) |
| --- | --- |
| Formula (5-1) compound | 5.00 |
| Reagent 1 | 4.50 |
| Reagent 2 | 3.40 |

Example 10

Fading Evaluation 2

The Formula (8-1) compound, Reagent 1, and Reagent 2, which were used in EXAMPLE 8, were evaluated in terms of fading as in EXAMPLE 9 by being dissolved in fetal bovine serum. The results of the fading evaluation are shown in Table 2 below and FIG. 11.

Figure 11:
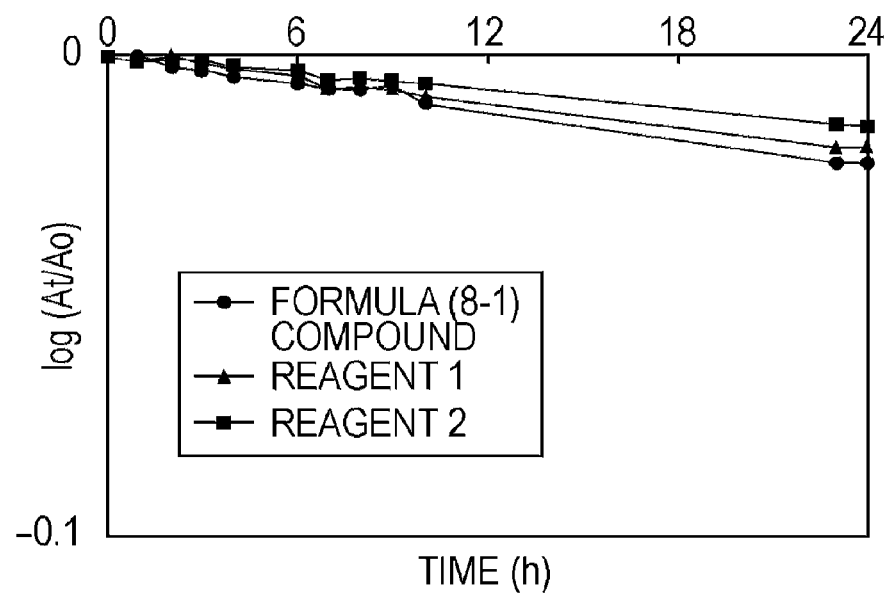
FIG. 11 is a graph showing the fading property of the compound represented by Formula (8-1) according to an embodiment of the present invention.

Referring to Table 2 and FIG. 11, the Formula (8-1) compound exhibited fading behavior similar to those of Reagent 1 and Reagent 2. This result suggests that the considerable decrease in the fluorescence intensity of the Formula (8-1) compound by the lapse of 24 hours from intravenous injection of the Formula (8-1) compound in EXAMPLE 8 is caused not by fluorescence fading but by rapid discharging of the Formula (8-1) compound from the biological system.

TABLE 2

| Compound | Fading rate (%) |
| --- | --- |
| Formula (8-1) compound | 5.2 |
| Reagent 1 | 4.5 |
| Reagent 2 | 3.4 |

Example 11

Tumor Imaging Evaluation 1

The Formula (5-1) compound obtained in EXAMPLE 1 was administered to tumor-transplanted-model mice and these mice were subjected to tumor imaging experiments. The tumor-transplanted-model mice were prepared by hypodermically transplanting a human gastric cancer cell line (hereinafter, referred to as N87), a human pancreatic cancer cell line (hereinafter, referred to as Suit2), and a human ovarian cancer cell line (hereinafter, referred to as SKOV3) in a cell concentration of $1 \times 10^6$ cells. The compound represented by Formula (5-1) in a concentration of 5 µM was administered to each tumor-transplanted-model mouse and, after the lapse of an hour, the mouse was subjected to tumor imaging by fluorescence imaging with IVIS (trademark) Imaging System. The evaluation results are shown in FIG. 12.

Figure 12:
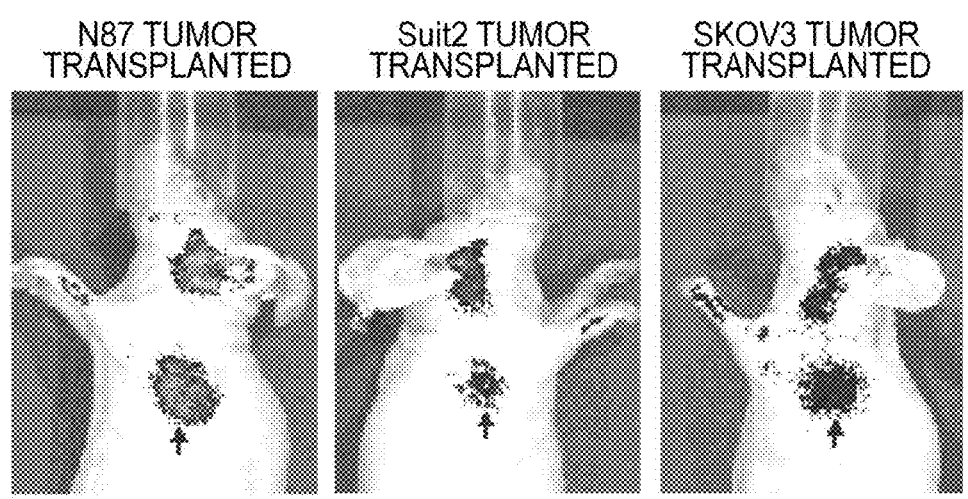
FIG. 12 shows images of results of imaging tumors in tumor-transplanted-model mice after the lapse of an hour from administration of the compound represented by Formula (5-1) according to an embodiment of the present invention to the mice.

Referring to FIG. 12, specific fluorescence signals were observed in tumor-transplanted sites (indicated by arrows in FIG. 12) after the lapse of an hour from administration of the Formula (5-1) compound. The size of the tumors was determined on the basis of the results of fluorescence imaging and the diameters of the tumors in the N87 tumor-transplanted-model mouse, the Suit2 tumor-transplanted-model mouse, and the SKOV3 tumor-transplanted-model mouse were respectively 6.8 mm, 3.3 mm, and 3.5 mm. Thus, the efficacy of the Formula (5-1) compound as a tumor contrast agent has been suggested.

Example 12

Tumor Imaging Evaluation 2

As in EXAMPLE 11, the compound represented by Formula (5-1) was administered in a concentration of 5 µM to a tumor-transplanted-model mouse to which SKOV3 tumor cells had been transplanted. The mouse was subjected to fluorescence imaging with IVIS (trademark) Imaging System and the diameter of a tumor was measured by tumor imaging. The diameter of the tumor was also measured with vernier calipers. The tumor was enucleated and the diameter of the enucleated tumor was also measured. The resultant three values of the diameter of the tumor were compared with each other. The results of measurements of the diameter of the tumor are summarized in Table 3 below.

The results in Table 3 show that a method of measuring the diameter of a tumor (a method according to the present invention) in which a compound according to the present invention is administered to a biological system and the tumor is imaged with the compound provides a value similar to that obtained by measuring the enucleated tumor. Thus, it has been suggested that a method according to the present invention is more effective than the measurement method with vernier calipers.

TABLE 3

| Tumor cell | Vernier caliper measurement (mm) | Method according to the present invention (mm) | Enucleated tumor measurement (mm) |
|---|---|---|---|
| SKOV3 | 5.3 | 3.5 | 3.3 |

Example 13

Fluorescence Kinetics Evaluation in Tumor-Bearing Site

The compound represented by Formula (5-1) and obtained in EXAMPLE 1 was administered to tumor-transplanted-model mice to which Suit2 tumor cells and N87 tumor cells had been transplanted in a manner similar to that in EXAMPLE 11. The tumor-bearing sites of these mice were evaluated in terms of fluorescence kinetics by fluorescence imaging. For comparison, fluorescence kinetics evaluations were also conducted in the same manner except that Reagent 1 and Reagent 2, which are marketed by Molecular Probes, Inc. and near-infrared fluorescence compounds, were used instead of the Formula (5-1) compound.

Figure 13:
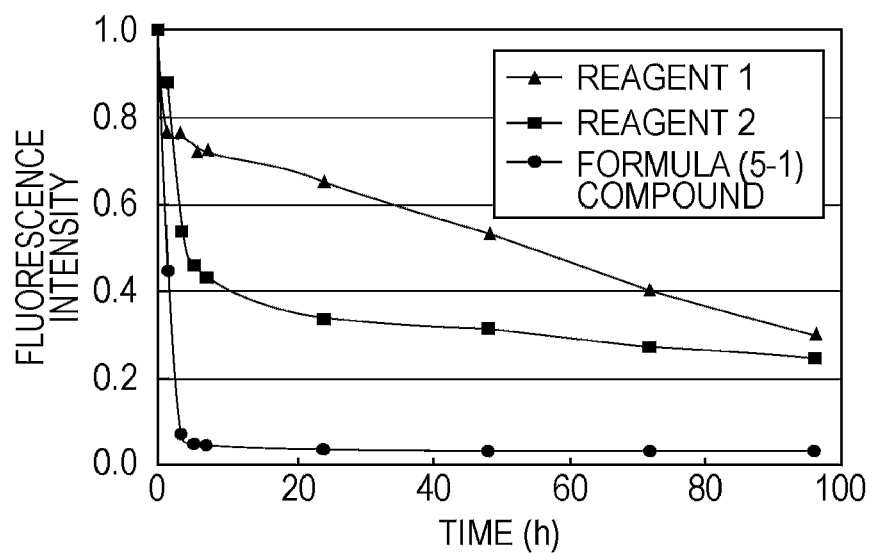
FIG. 13 is a graph showing, at a tumor-bearing site, variation in fluorescence intensity over time from administration of the compound represented by Formula (5-1) according to an embodiment of the present invention to a Suit2-tumor-transplanted-model mouse to the lapse of 96 hours.
Figure 14:
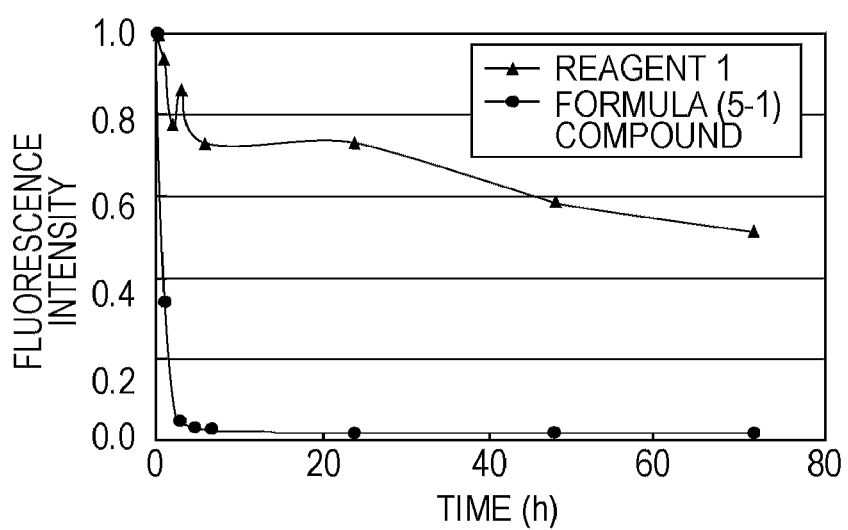
FIG. 14 is a graph showing, at a tumor-bearing site, variation in fluorescence intensity over time from administration of the compound represented by Formula (5-1) according to an embodiment of the present invention to a N87-tumor-transplanted-model mouse to the lapse of 72 hours.

Specifically, 200 µL PBS solutions (concentration: 5 µM) of the Formula (5-1) compound, Reagent 1, and Reagent 2 were intravenously injected into the tails of the tumor-transplanted-model mice. The fluorescence intensity of the resultant tumor-bearing sites was determined over time with IVIS (trademark) Imaging System. The fluorescence intensity after the lapse of 15 minutes from the injection was defined as 1 and the fluorescence intensity over time was relatively plotted in terms of the tumor-transplanted-model mice to which Suit2 tumor cells and N87 tumor cells had been transplanted. The results are shown in FIGS. 13 and 14. In this fluorescence measurement, the mice were anesthetized by inhalation. The evaluation was conducted after the NHS groups of Reagent 1 and Reagent 2 were deactivated with glycin.

Referring to FIGS. 13 and 14, after the lapse of 5 hours from intravenous injection of the compound represented by Formula (5-1), the fluorescence intensity of the Formula (5-1) compound at the tumor-bearing sites decreased to a level before administration of the Formula (5-1) compound. The fluorescence intensity of the Formula (5-1) compound rapidly decreased compared with Reagent 1 and Reagent 2 administered as comparative examples. The Formula (5-1) compound did not exhibit fluorescence accumulation specific to tumors.

The fluorescence intensity over time at the tumor-bearing sites to which Suit2 tumor cells and N87 tumor cells had been transplanted is summarized in Table 4 below as relative values with respect to the fluorescence intensity before the injection being defined as 1. Referring to Table 4, after the lapse of 7 hours from the injection of the Formula (5-1) compound, the relative values of the Formula (5-1) compound had decreased to 1.5 or less, which is within 150% of the fluorescence intensity before administration of the Formula (5-1) compound. In contrast, in the tumor-transplanted-model mouse to which Reagent 1 was administered, 7 hours after the administration, the fluorescence intensity on the surface of the mouse had not decreased to the background level.

The results suggest that the Formula (5-1) compound is eliminated rapidly from tumor-bearing sites after functioning as a contrast agent for tumors. The results suggest the possibility that the Formula (5-1) compound is rapidly discharged from biological systems compared with Reagent 1 and Reagent 2 serving as comparative examples.

TABLE 4

| Elapsed time after administration | Suit2 transplanted/ Formula (5-1) compound | N87 transplanted/ Formula (5-1) compound | Suit2 transplanted/ Reagent 1 |
|---|---|---|---|
| 0 | 1.0 | 1.0 | 1.0 |
| 15 minutes | 52.5 | 50.8 | 34.1 |
| 1 hour | 18.1 | 17.1 | 26.2 |
| 3 hours | 2.6 | 1.6 | 26.3 |
| 5 hours | 1.7 | N.A. | 24.5 |
| 7 hours | 1.5 | 1.4 | 24.7 |
| 1 day | 1.2 | 1.1 | 22.4 |
| 2 days | 1.1 | 1.0 | 18.1 |
| 3 days | 1.1 | 1.0 | 13.7 |

N.A.: no data

The present invention can provide a compound that is rapidly discharged from biological systems. The present invention can also provide a compound containing a labeled substance being fixed to the compound for the purpose of providing selectivity for an imaging target site. Such a compound containing a labeled substance being fixed according to the present invention can be used as a labeling agent for photonic imaging.

According to the present invention, after the lapse of certain time from administration of a contrast agent, various medicaments such as other contrast agents or therapeutic agents can be administered. Thus, the present invention can also provide a method that allows tracking of variation in the diameter of a tumor over time, evaluation of the efficacy of a medicament, a test, or the like.

While the present invention has been described with reference to exemplary embodiments, it is to be understood that

What is claimed is:

1. A A composition comprising a contrast agent for fluorescence imaging or photoacoustic imaging, the contrast agent comprising the compound represented by Formula (1) below,

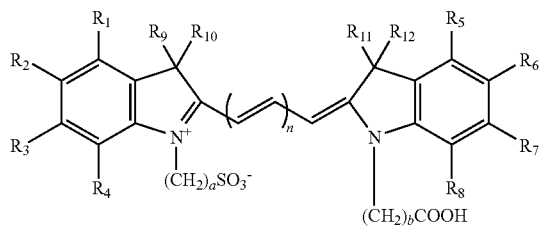

Formula (1)

where n is 2; a is an integer of 1 to 3 and b is an integer of 3 and 5 to 10, or a is 4 and b is an integer of 3 and 6 to 10, or a is 5 and b is an integer of 1 to 10;

where n is 3; a is an integer of 1 to 4 and b is an integer of 3 and 5 to 10, or a is 5 and b is an integer of 1 to 10;

$R_1$ to $R_8$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; and $R_9$ to $R_{12}$ each independently represent a substituted or unsubstituted C1-C3 alkyl group.

2. A compound represented by Formula (2) below,

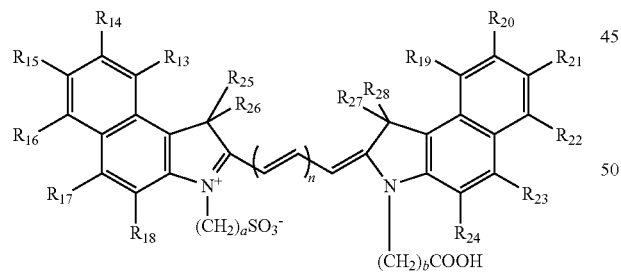

Formula (2)

where n is 2 or 3; a is an integer of 1 to 4 and b is an integer of 3 and 5 to 10, or a is 5 and b is an integer of 1 to 10, with a case where n is 2, a is 4, and b is 5; a case where n is 3, a is 3, and b is 5; and a case where n is 3, a is 4, and b is 5, being excluded; $R_{13}$ to $R_{24}$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; and $R_{25}$ to $R_{28}$ each independently represent a substituted or unsubstituted C1-C3 alkyl group; where n is 2; at least one of $R_{13}$ to $R_{24}$ is a sulfonate that is any one of sodium sulfonate, potassium sulfonate, ammonium sulfonate, triethylammonium sulfonate, pyridinium sulfonate, lysine sulfonate, and arginine sulfonate.

3. A probe represented by Formula (3) below,

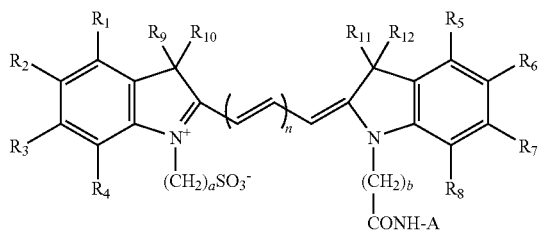

Formula (3)

where n is 2 or 3; a and b each represent an integer of 1 to 10; $R_1$ to $R_8$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; $R_9$ to $R_{12}$ each independently represent a substituted or unsubstituted C1-C3 alkyl group;

and A represents a molecular recognition compound.

4. A probe represented by Formula (4) below,

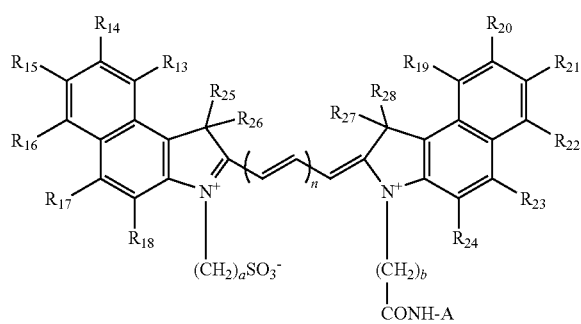

Formula (4)

where n is 2 or 3; a and b each represent an integer of 1 to 10; $R_{13}$ to $R_{24}$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; $R_{25}$ to $R_{28}$ each independently represent a substituted or unsubstituted C1-C3 alkyl group; and A represents a molecular recognition compound.

5. A compound represented by Formula (5) below,

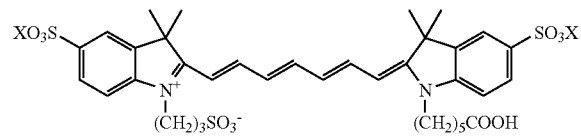

Formula (5)

where each $SO_3X$ represents any one of sodium sulfonate, potassium sulfonate, ammonium sulfonate, triethylammonium sulfonate, pyridinium sulfonate, lysine sulfonate, and arginine sulfonate.

6. A compound represented by Formula (6) below,

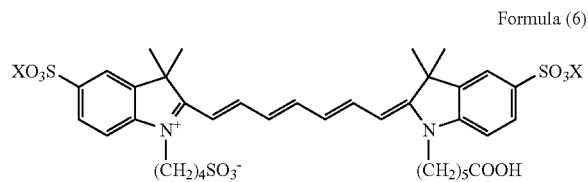

Formula (6)

where each SO$_3$X represents any one of sodium sulfonate, potassium sulfonate, ammonium sulfonate, triethylammonium sulfonate, pyridinium sulfonate, lysine sulfonate, and arginine sulfonate.

7. A compound represented by Formula (7) below,

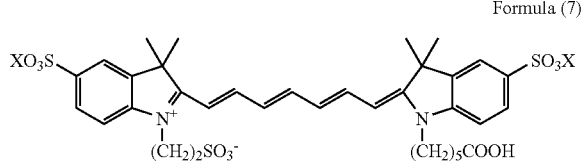

Formula (7)

where each SO$_3$X represents any one of sodium sulfonate, potassium sulfonate, ammonium sulfonate, triethylammonium sulfonate, pyridinium sulfonate, lysine sulfonate, and arginine sulfonate.

8. A compound represented by Formula (8) below,

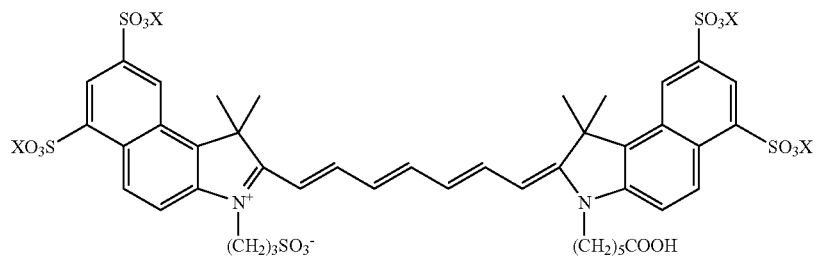

Formula (8)

where each SO$_3$X represents any one of sodium sulfonate, potassium sulfonate, ammonium sulfonate, triethylammonium sulfonate, pyridinium sulfonate, lysine sulfonate, and arginine sulfonate.

9. A compound represented by Formula (1) below,

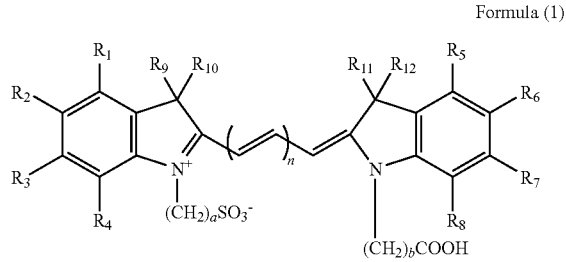

Formula (1)

where n is 2 or 3; a is an integer of 1 to 4 and b is an integer of 3 and 5 to 10, or a is 5 and b is an integer of 1 to 10; at least any two of R$_1$ to R$_8$ each are a sulfonate that is any one of sodium sulfonate, potassium sulfonate, ammonium sulfonate, triethylammonium sulfonate, pyridinium sulfonate, lysine sulfonate, and arginine sulfonate, and the rest of R$_1$ to R$_8$ each are a hydrogen atom; and R$_9$ to R$_{12}$ each independently represent a substituted or unsubstituted C1-C3 alkyl group.

10. A compound represented by Formula (2) below,

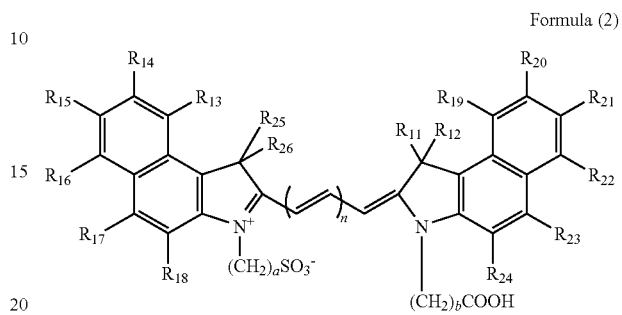

Formula (2)

where n is 2 or 3; a is an integer of 1 to 4 and b is an integer of 3 and 5 to 10, or a is 5 and b is an integer of 1 to 10, with a case where n is 2, a is 4, and b is 5; a case where n is 3, a is 3, and b is 5; and a case where n is 3, a is 4, and b is 5, being excluded; at least any four of R$_{13}$ to R$_{24}$ each are a sulfonate that is any one of sodium sulfonate, potassium sulfonate, ammonium sulfonate, triethylammonium sulfonate, pyridinium sulfonate, lysine sulfonate, and arginine sulfonate, and the rest of R$_{13}$ to R$_{24}$ each are a hydrogen atom; and R$_{25}$ to R$_{28}$ each independently represent a substituted or unsubstituted C1-C3 alkyl group.

11. A probe represented by Formula (4) below,

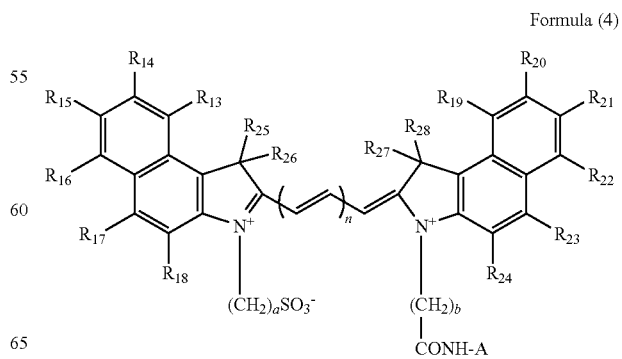

Formula (4)

where n is 2 or 3; a and b each represent an integer of 1 to 10; $R_{13}$ to $R_{24}$ each independently represent a hydrogen atom or a sulfonate that is any one of sodium sulfonate, potassium sulfonate, ammonium sulfonate, triethylammonium sulfonate, pyridinium sulfonate, lysine sulfonate, and arginine sulfonate; $R_{25}$ to $R_{28}$ each independently represent a substituted or unsubstituted C1-C3 alkyl group; and A represents a molecular recognition compound;

where n is 2; at least one of $R_{13}$ to $R_{24}$ is a sulfonate that is any one of sodium sulfonate, potassium sulfonate, ammonium sulfonate, triethylammonium sulfonate, pyridinium sulfonate, lysine sulfonate, and arginine sulfonate.

12. A contrast agent for fluorescence imaging, the contrast agent containing the compound according to claim 2.

13. A fluorescence imaging method including detection of an existing position of a compound in a biological system, the method comprising:
    preparing the compound;
    administering a contrast agent for fluorescence imaging or photoacoustic imaging comprising the compound to the biological system;
    irradiating the biological system with light; and
    detecting fluorescence emitted from the compound existing in the biological system,
    wherein the contrast agent is the contrast agent according to claim 1 comprising the compound represented by Formula (1).

14. A fluorescence imaging method including detection of an existing position of a compound in a biological system, the method comprising:
    preparing the compound;
    administering the compound to the biological system;
    irradiating the biological system with light; and
    detecting fluorescence emitted from the compound existing in the biological system,
    wherein the compound is the compound according to claim 2.

15. A fluorescence imaging method including detection of an existing position of a probe in a biological system, the method comprising:
    preparing the probe;
    administering the probe to the biological system;
    irradiating the biological system with light; and
    detecting fluorescence emitted from the probe existing in the biological system,
    wherein the probe is the probe according to claim 3.

16. A fluorescence imaging method including detection of an existing position of a probe in a biological system, the method comprising:
    preparing the probe;
    administering the probe to the biological system;
    irradiating the biological system with light; and
    detecting fluorescence emitted from the probe existing in the biological system,
    wherein the probe is the probe according to claim 4.

* * * * *